United States Patent [19]

Kobayashi et al.

[11] Patent Number: 4,948,736

[45] Date of Patent: Aug. 14, 1990

[54] CONTINUOUS MICROORGANISM CULTIVATING APPARATUS

[75] Inventors: Takeshi Kobayashi, Nagoya; Masayuki Taniguchi, Niigata; Shunji Yasuda, Funabashi; Shigehito Ikeda, Tougane, all of Japan

[73] Assignee: Toshiba Ceramics Co., Ltd., Tokyo, Japan

[21] Appl. No.: 373,595

[22] Filed: Jun. 30, 1989

Related U.S. Application Data

[63] Continuation of Ser. No. 28,270, Mar. 20, 1987, abandoned.

[51] Int. Cl.⁵ .............................................. C12M 1/12
[52] U.S. Cl. .................... 435/311; 435/286; 435/813; 210/275; 210/510.1
[58] Field of Search .............. 435/284, 286, 311, 316, 435/813; 210/275, 411, 510.1

[56] References Cited

U.S. PATENT DOCUMENTS

| | | | |
|---|---|---|---|
| 2,618,565 | 11/1952 | Nicholson | 210/510.1 |
| 3,126,333 | 3/1964 | Williams | 210/275 |
| 3,923,654 | 12/1975 | O'Hern et al. | 210/510.1 |
| 4,130,486 | 12/1978 | Dyer et al. | 210/411 |
| 4,587,016 | 5/1986 | Sumiyoshi | 210/510.1 |
| 4,647,376 | 3/1987 | Galaj | 210/510.1 |
| 4,698,157 | 10/1987 | Gillot | 210/510.1 |

FOREIGN PATENT DOCUMENTS 55-54890  4/1980  Japan .
58-34006  2/1983  Japan .
58-196818 11/1983 Japan .
59-52511  3/1984  Japan .

OTHER PUBLICATIONS

Testing Tubular Crossflow Modules, Ceraflo Asymmetric Ceramic Microfilters, 1984.
Ethanol Production by Cell Recycling with Hollow Fibers, J. Ferment Technol., Y. Nishizawa et al., vol. 61, No. 6, pp. 599-605 1983.
C. Guizard et al., Nouvelles Membranes Minerales d'Ultrafiltration Application a la Purification de L'Eau, Le Lait, 64, pp. 276-285, 1984.
M. Dostalek et al., A Filter Fermenter—Apparatus and Control Equipment, Biotech. & Bioengineering, vol. XXIV, pp. 2077-2086, 1982.
D. E. Brown et al., A New Filter for Cell Separation, Biotechnology Letters, vol. 6, No. 6, pp. 401-406, 1984.
The Society of Chemical Engineers, Japan, pp. 316, 317, 333, 1984.

Primary Examiner—Noah P. Kamen
Attorney, Agent, or Firm—Wegner & Bretschneider

[57] ABSTRACT

A continuous microorganism cultivating apparatus has a stock solution tank which receives a stock solution for a microbial reaction and is provided with a cylindrical filter through which the stock solution is passed. The stock solution is separated by the filter into filtrate containing a metabolic product and concentrated liquid containing microbes. The concentrated liquid is then recycled to the stock solution. The filter is a ceramic filter having a multitude of pores, which is connected to a back wash device.

5 Claims, 2 Drawing Sheets

CONTINUOUS MICROORGANISM CULTIVATING APPARATUS

This application is a continuation of U.S. application Ser. No. 028,270, filed Mar. 20, 1987, now abandoned.

BACKGROUND OF THE INVENTION

The present invention relates to an improvement in a continuous microorganism cultivating apparatus.

In producing a useful material using a continuous microorganism cultivating apparatus which utilizes a metabolic function of microorganisms, it is necessary not only to maintain the concentration of microorganisms (microbes) in a reaction vessel at a high level but also removes metabolic products which will impede the growth of the microbes, in order to improve productivity.

As methods for maintaining the microbial concentration at a high level there are known, for example, a method in which microbes are precipitated and agglutinated, and a method in which microbes are immobilized. However, these methods are often impractical because a long time is required.

In view of this impracticality in the prior art, filters have been used for separating microbes and a metabolic product from each other continuously over a relatively short time. Examples of such filters include sintered tungsten tubes, unglazed ceramic supports coated with diatomaceous earth, and hollow fibers made of a synthetic resin. The problems with these filters are whether they are durable, stable over a long period, or re-employable. Particularly, it is questionable whether these filters can be back washed for avoiding plugging up of the filters by microbes or whether they can be cleaned by heat sterilization for reuse.

On this regard, a sintered tungsten tube is easily corroded by acid and is not suitable for back wash. In the case of a filter constituting by a ceramic support coated with diatomaceous earth, it is impossible to effect back washing, since the ceramic material serving as the support is coarse, having a pore diameter in the range of 10 to 50 $\mu$m. This is because the ceramic material need not have a separating function. Further, a hollow fiber made of a synthetic resin does not permit back wash or heat sterilization and permits only a small treatment volume.

SUMMARY OF THE INVENTION

It is an object of the present invention to provide a continuous microorganism cultivating apparatus capable of being back washed and heat sterilized.

In the continuous microorganism cultivating apparatus according to the present invention, a stock solution for microbial reaction is passed through a cylindrical filter to separate it into a filtrate which contains a metabolic product and a concentrated liquid containing microbes. This concentrated liquid is then recycled to the stock solution. A ceramic filter having a multitude of pores is used, and a back wash device is connected to the ceramic filter.

In such a continuous microorganism cultivating apparatus, the ceramic filter has high mechanical strength and heat resistance, so it is possible to back wash and heat sterilize the filter, thus permitting stable use of the filter over a long period of time and also permitting re-use of the filter.

It is desirable that this ceramic filter have a pore diameter in the range of 0.2 to 10 $\mu$m. This is because if the pore diameter is smaller than 0.2 $\mu$m, the flux of filtrate from the filter is small and so productivity is reduced, while if it exceeds 10 $\mu$m, the microbes will leak into the filtrate.

DETAILED DESCRIPTION OF THE INVENTION

Figure 1:
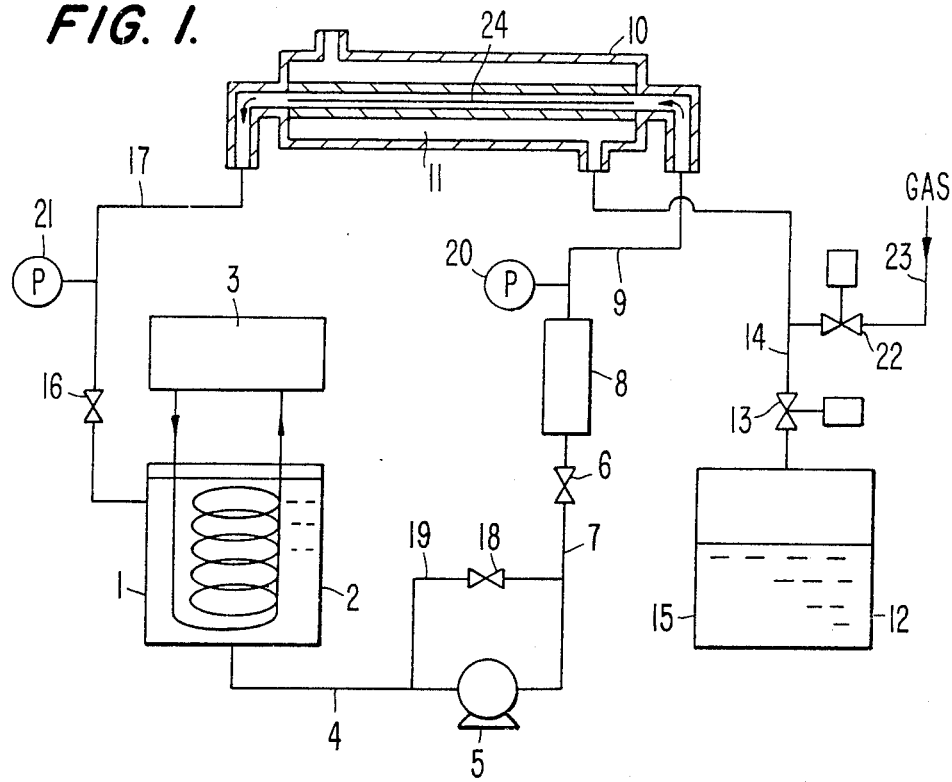
FIG. 1 is a schematic block diagram of a continuous microorganism cultivating apparatus according to an embodiment of the present invention.

In FIG. 1, a stock solution 2 which contains bread yeast, *Escherichia coli*, or other microorganisms in a suspended or cultivated state is charged into a stock solution tank 1. The stock solution 2 is maintained at a constant temperature by constant temperature water fed through coils from a constant temperature bath 3. The stock solution 2 passes through a pipe 4, a pump 5, a pipe 7 with a ball valve 6 mounted therein, a flow meter 87 and an inlet pipe 9 and then passes through a cylindrical ceramic filter 11 provided within a filter case 10. Filtrate 12 obtained through the Ceramic filter 11 and containing metabolic products passes through a filtrate pipe 14 with a solenoid valve 13 mounted therein and is stored in a filtrate tank 15. On the other hand, concentrated liquid containing microbes is recycled to the stock solution tank 1 through an outlet pipe 17 with a ball valve 16 mounted therein. Between the pipes 4 and 7 is connected, in parallel with the pump 4, a reflux by-passed pipe 19 with a ball valve 18 mounted therein. Further, to the filtrate pipe 14 is connected a gas feed pipe 23 for back washing with a solenoid valve 22 mounted therein.

As the ceramic filter 11 was used a filter formed of a high purity alumina and having a multi-layer structure in which the pore diameter gradually becomes larger from the inner surface toward the outer surface. The filter had an inside diameter of 15 mm, an outside diameter of 19 mm and a length of 250 mm.

In this apparatus, since a back wash device is connected to the ceramic filter 11, it is possible to prevent lowering of the filtration efficiency caused by plugging up of the filter. Further, the ceramic filter 11 can be removed, heat-sterilized and re-used when cultivation of another kind of microbe is to be carried out or when the culture medium has been contaminated. Consequently, it is possible to obtain a metabolic product continuously and efficiently.

A test was carried out using this apparatus to determine the influence of pore diameter at the inner surface of the ceramic filter 11 upon the filtration flux of a suspension of *Escherichia coli* C600. In this experiment there were used three kinds of ceramic filters, having pore diameters of 0.2, 0.5 and 1.5 $\mu$m, respectively, at the inner surface. The filter inlet pressure and the flow rate were set at 0.6 kg/cm³ and 3×10⁻³ m³/min, respectively. The results are shown in FIG. 2.

Figure 2:
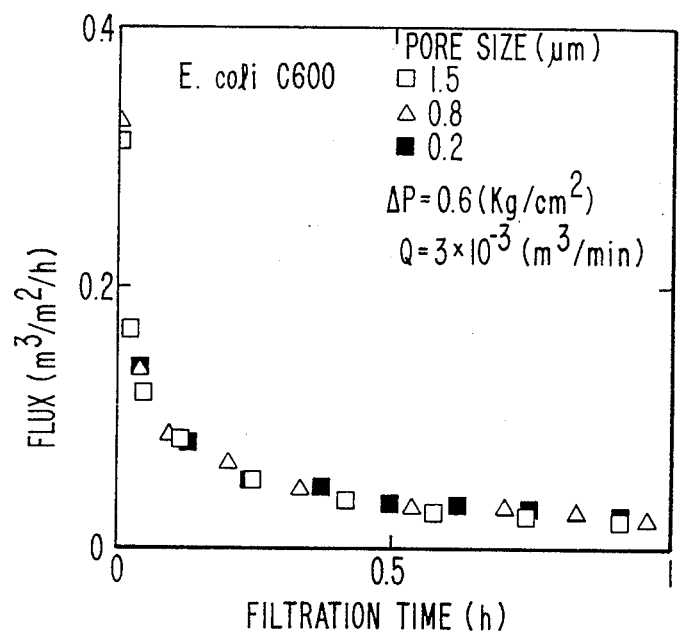
FIG. 2 is a diagram illustrating the relation between filter pore diameters and filtration flux in filtration performed using the above apparatus.

A look at FIG. 2 shows that in the ceramic filters having pore diameters of 0.2, 0.5 and 1.5 μm, the pore diameters exert no influence upon filtration flux. However, the filtration flux suddenly dropped in 10 minutes after the start of the filtration and reached an approximately constant level after 30 minutes. The flux at that time was about one tenth of the initial value. Such a change in filtration flux is believed to arise from the formation of microbial cake on the ceramic filter surface owing to the small liquid flow velocity. Therefore, it is considered necessary to enlarge the liquid flow velocity in order to attain so-called cross flow filtration, which does not permit the formation of microbial cake.

Next, a test was carried out to determine the influence of liquid flow velocities upon the filtration flux in the filtration of a suspension of 100 g/l bread yeast performed using the ceramic filter having a 1.5 μm pore diameter in the above apparatus. The results are as shown in FIG. 3.

Figure 3:
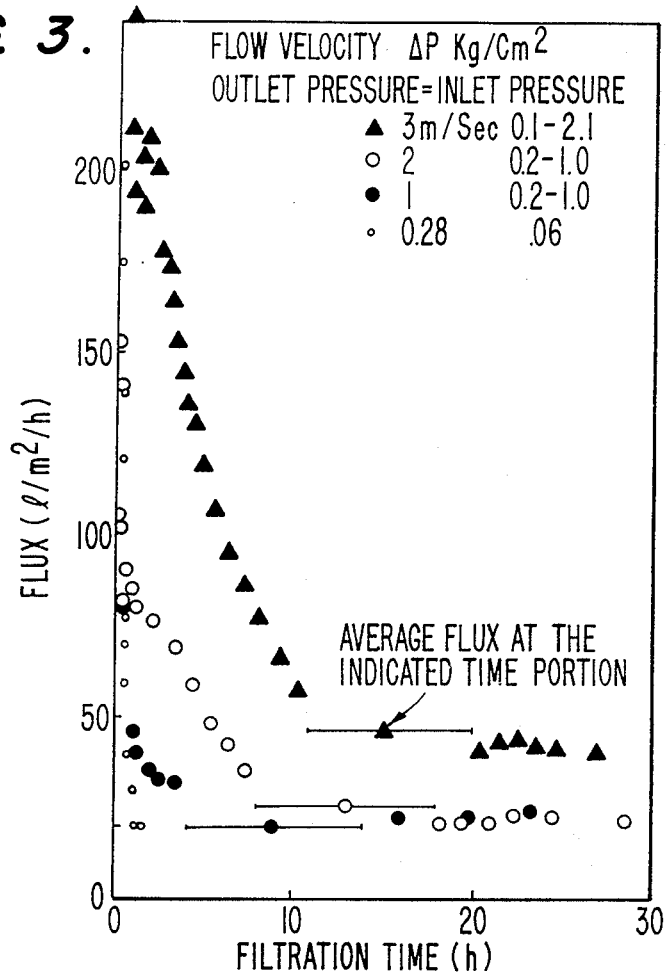
FIG. 3 is a diagram illustrating the relation between liquid flow velocities and filtration flux in filtration performed using the above apparatus.

As is apparent from FIG. 3, it was confirmed that the lowering of filtration flux could be suppressed to a remarkable extent by increasing the liquid flow velocity. from this result it is expected that an increase in liquid flow velocity will lead to a decrease in the number of times back washing is needed.

Figure 4:
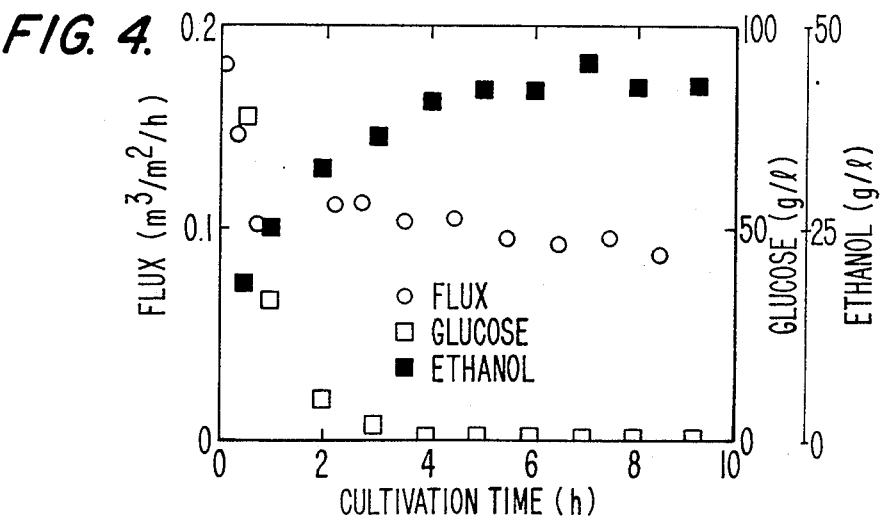
FIG. 4 is a diagram showing productivity in alcoholic fermentation with bread yeast using the above apparatus.

Further, using the above apparatus and also using a culture medium containing 10% glucose, ethanol fermentation with bread yeast was performed. As a result, the flux of filtrate as well as the concentrations of ethanol and glucose were found to be as shown in FIG. 4. In this experiment there was used the ceramic filter having a 1.5 μm pore diameter, and the same pressure and flow rate conditions as in FIG. 2 were adopted. Further, in order to prevent the lowering of filtration flux, back wash was performed using nitrogen gas at 5 atm for 5 seconds every 5 minutes.

As is apparent from FIG. 4, there was no remaining glucose detected 4 hours after the start of the cultivation, and ethanol was obtained at a rate of 90% of the theoretical yield. Little leakage of microbes was observed throughout the incubation period.

Although an alumina filter was used as the ceramic filter in the above embodiment, there may be used a filter of another material such as, for example, silicon carbide or silicon nitride. The pore diameter of the ceramic filter may be selected suitably according to the size and shape of microorganism. Moreover, a liquid flow control means 24 having a spiral, rod-like or any other shape may be inserted into the ceramic filter to enhance the cross flow effect.

Further, the continuous microorganism cultivating apparatus of the present invention can be used for all microbial reactions, e.g. acetone-butanol fermentation, cultivation of microorganisms such as lactic acid bacteria (including *Lactobacillus bifidus*), cultivation and concentration of gene recombination host bacteria such as *E. coli* C600 and *E. coli* HB101, in addition to alcohol fermentation. It is also employable for the production of antibodies using animals and plants.

By using the continuous microorganism cultivating apparatus of the present invention outstanding effects are attained. For example, a metabolic product can be stably obtained by a microbial reaction over a long period of time.

We claim:

1. A continuous microorganism cultivating apparatus comprising:
   a stock solution tank containing a stock solution for microbial reaction;
   a filter casing;
   a pipe connecting the stock solution tank with the filter casing;
   a cylindrical filter through which the stock solution can pass in the longitudinal direction of the filter, the filter being placed within the filter casing in such a manner which provides cross-filtration so that the stock solution fed from the stock solution tank passes through the filter, thus separating the stock solution into a filtrate containing a metabolic product and a concentrated liquid containing microbes;
   means placed between the filter casing and the stock solution tank for recycling the concentrated liquid from the filter casing into the stock solution tank;
   a filtrate tank for storing the filtrate;
   a filtrate pipe for connecting the filter casing with the filtrate tank so as to feed the filtrate from the filter casing into the filtrate tank;
   a gas feed pipe joined to the filtrate pipe for feeding a gas through the filtration pipe into the filter casing and back-washing the filter within the filter casing;
   temperature control means for keeping the stock solution contained within the stock solution tank at a constant temperature, comprising a constant-temperature bath and means for feeding a constant-temperature water from the bath through coils in the stock solution in such a manner that the stock solution is maintained at a constant temperature by the constant-temperature water; and 'a valve and a flow meter for controlling pressure and flow rate of the solution;
   wherein the filter, made of a high purity alumina, has a multi-layer structure in which the pore diameters gradually increase from an inner surface of the filter to an outer surface of the filter and the pores have an average pore diameter ranging between 0.2 microns and 1.5 microns, and wherein a liquid flow control means is inserted into the ceramic filter to enhance the cross flow effect.

2. A continuous microorganism cultivating apparatus as defined in claim 1, wherein the gas is nitrogen gas.

3. A continuous microorganism cultivating apparatus as defined in claim 1, wherein the stock solution contains bread yeast or *Escherichia coli*.

4. A continuous microorganism cultivating apparatus as defined in claim 1, further comprising:
   means for controlling the flow velocity of the stock solution at a value so as to attain cross-flow filtration which does not permit the formation of microbial cake.

5. A continuous microorganism cultivating apparatus comprising:
   a stock solution tank capable of containing a stock solution for microbial reaction;
   a filter casing;
   a pipe connecting the stock solution tank with the filter casing;
   a cylindrical filter through which the stock solution can pass in the longitudinal direction of the filter, the filter being placed within the filter casing in such a manner which provides cross-filtration so that the stock solution fed from the stock solution tank passes through the filter, thus separating the stock solution into a filtrate containing a metabolic product and a concentrated liquid containing microbes;

means placed between the filter casing and the stock solution tank for recycling the concentrated liquid from the filter casing into the stock solution tank;

a filtrate tank for storing the filtrate;

a filtrate pipe for connecting the filter casing with the filtrate tank so as to feed the filtrate from the filter casing into the filtrate tank;

a gas feed pipe joined to the filtrate pipe for feeding a gas through the filtration pipe into the filter casing and backwashing the filter within the filter casing;

temperature control means for keeping the stock solution contained within the stock solution tank at a constant temperature, comprising a constant-temperature bath and means for feeding a constant-temperature water from the bath through coils in the stock solution in such a manner that the stock solution is maintained at a constant temperature by the constant-temperature water; and a valve and a flow meter for controlling pressure and flow rate of the solution;

wherein the filter, made of a high purity alumina, has a multi-layer structure in which the pore diameters gradually increase from an inner surface of the filter to an outer surface of the filter and the pores have an average pore diameter ranging between 0.2 microns and 1.5 microns, and wherein a liquid flow control means is inserted into the ceramic filter to enhance the cross flow effect.

* * * * *